United States Patent [19]

Blanchard

[11] Patent Number: 6,028,189
[45] Date of Patent: Feb. 22, 2000

[54] SOLVENT FOR OLIGONUCLEOTIDE SYNTHESIS AND METHODS OF USE

[75] Inventor: Alan P. Blanchard, Seattle, Wash.

[73] Assignee: University of Washington, Seattle, Wash.

[21] Appl. No.: 08/821,156

[22] Filed: Mar. 20, 1997

[51] Int. Cl.[7] .................... C07H 21/00; C07H 21/02; C07H 21/04

[52] U.S. Cl. ................. 536/25.3; 536/23.1; 536/24.3; 422/131

[58] Field of Search ................. 536/23.1, 24.3, 536/25.3; 422/131

[56] References Cited

U.S. PATENT DOCUMENTS

| | | | |
|---|---|---|---|
| 4,689,405 | 8/1987 | Frank et al. | 536/27 |
| 4,877,745 | 10/1989 | Hates et al. | 436/166 |
| 4,940,760 | 7/1990 | Boettcher et al. | 526/190 |
| 5,036,081 | 7/1991 | Cozzette et al. | 427/2 |
| 5,047,524 | 9/1991 | Andrus et al. | 536/27 |
| 5,063,081 | 11/1991 | Cozzette et al. . | |
| 5,112,974 | 5/1992 | Barton | 546/4 |
| 5,124,444 | 6/1992 | Van Ness et al. | 536/27 |
| 5,130,369 | 7/1992 | Hughes et al. | 524/846 |
| 5,143,854 | 9/1992 | Pirrung et al. . | |
| 5,149,798 | 9/1992 | Agrawal et al. | 536/27 |
| 5,157,032 | 10/1992 | Barton | 514/185 |
| 5,200,051 | 4/1993 | Cozzette et al. | 204/403 |
| 5,212,050 | 5/1993 | Mier et al. | 430/320 |
| 5,252,743 | 10/1993 | Barrett et al. . | |
| 5,318,679 | 6/1994 | Nishioka . | |
| 5,319,080 | 6/1994 | Leumann | 536/27.1 |
| 5,378,638 | 1/1995 | Deeg et al. . | |
| 5,436,327 | 7/1995 | Southern . | |
| 5,449,754 | 9/1995 | Nishioka . | |
| 5,474,796 | 12/1995 | Brennan | 427/2.13 |
| 5,552,270 | 9/1996 | Khrapko et al. . | |
| 5,658,802 | 8/1997 | Hayes et al. . | |
| 5,700,637 | 12/1997 | Southern . | |
| 5,733,509 | 3/1998 | Ackley et al. | 422/131 |
| 5,747,058 | 5/1998 | Tipton et al. | 424/423 |
| 5,763,170 | 6/1998 | Raybuck | 435/6 |

FOREIGN PATENT DOCUMENTS

| | | | |
|---|---|---|---|
| 59024244 | 2/1984 | Japan . | |
| WO 89/10977 | 11/1989 | WIPO . | |
| WO 90/00626 | 1/1990 | WIPO . | |
| WO 92/10588 | 6/1992 | WIPO . | |
| WO 93/17126 | 9/1993 | WIPO . | |
| WO 94/01215 | 1/1994 | WIPO . | |
| WO 94/27719 | 12/1994 | WIPO . | |
| WO 95/11748 | 5/1995 | WIPO | B01Y 19/00 |
| WO 95/25116 | 9/1995 | WIPO . | |
| WO 95/35505 | 12/1995 | WIPO . | |
| WO 97/19749 | 6/1997 | WIPO . | |
| WO 97/44134 | 11/1997 | WIPO . | |
| WO9744134 | 11/1997 | WIPO . | |
| WO 98/10858 | 3/1998 | WIPO . | |
| WO 98/25944 | 6/1998 | WIPO . | |

OTHER PUBLICATIONS

Blanchard et al., Biosensors & Bioelectronics 11(6/7):687–690 (1996).

Atkinson and Smith, "Solid Phase Synthesis of Oligodeoxyribonucleosides by the Phosphitetriester Method," *Oligonucleotide Synthesis*, M.J. Gait, ed., Oxford IRL Press, pp. 35–39 (1984).

Blackburn and Gait (eds.), *Nucleic Acids in Chemistry and Biology*, Second Edition, New York: Oxford University Press (1996).

Brennen, "Sequencing by Hybridization: Methods to Generate Large Arrays of Oligonucleotides", Human Genome Program, U.S. Department of Energy, Contractor–Grantee Workshop III, Feb. 7–10, 1993, p. 92. (1993).

Gait, "Solid–phase Synthesis of Oligodeoxyribo–nucleotides by the Phosphotriester Method," *Oligonucleotide Synthesis*, M.J. Gait, ed., Oxford IRL Press, pp. 83–111 (1984).

Geysen et al., "Strategies for Epitope Analysis Using Peptide Synthesis, " *J. Immunol. Meth.* 102:259–274 (1987).

Kaumaya et al., "Synthesis and Biophysical Characterization of Engineered Topographic Immunogenic Determinants with αα Topology," *Biochem.* 29:13–23 (1990).

Lam et al., "A New Type of Synthetic Peptide Library for Identifying Ligand–Binding Activity," *Nature* 354:82–84 (1991).

Ramalho et al., "Introduction to Solid–Phase Oligonucleotide Chemistry," Interactiva Virtuelles Labor, http://www.interactive.de/oligoman/intro inh.html.

Weiler et al., "Combining the Preparation of Oligonucleotide Arrays and Synthesis of High–Quality Primers," *Anal. Biochem.* 243:218–227 (1996).

Lemmo et al., "Characterization of an Inkjet Chemical Microdispenser or Combinatorial Library Synthesis," *Anal. Chem.*, 69:543–551 (1997).

O'Donnell–Maloney and Little, "Microfabrication and array technologies for DNA sequencing and diagnostics," *Genetic Analysis: Biomolecular Engineering*, 13:151–157 (1996).

Kirk–Othmer, "Silver to Sulfolanes and Sulfones," *Encyclopedia of Chemical Technology*, 3rd Edition, 21:378–391.

Habus et al., Nucleic Acids Research 22(20 : 4350–4351 (1994).

Goodchild, Bioconjugate Chemistry 1(3) : 165–187 (1990).

Miller, Bioconjugate Chemistry 1(3) : 187–191 (1990).

Dahl et al., Nucleic Acids Research 15(4):1729–1743 (1987).

Blanchard et al., "High–density oligonucleotide arrays" *Biosensors & Bioelectronics* 11 (6/7) :687–690 (1996).

(List continued on next page.)

*Primary Examiner*—Stephanie W. Ztomer
*Assistant Examiner*—Ethan Whisenant
*Attorney, Agent, or Firm*—Campbell & Flores LLP

[57] ABSTRACT

The invention provides methods for assembling arrays of oligonucleotides on a solid support, wherein the arrays can optionally be removed from the support after assembly. The invention also provides a solvent suitable for automated assembly of arrays of oligonucleotides.

8 Claims, 3 Drawing Sheets

OTHER PUBLICATIONS

Blanchard and Hood, "Oligonucleotide Array Synthesis Using Ink Jets" Eighth International Genome Sequencing and Analysis Conference, TIGR Science Education Foundation, Inc. (Oct. 5–8, 1996).

Chen et al., "Synthesis of oligodeoxyribonucleotide N3'→P5' phosphoramidates" *Nucleic Acids Research* 23(14):2661–1668 (1995).

Froehler et al., "Synthesis of DNA via deoxynucleoside H–phosphonate intermediates" *Nucleic Acids Res.* 14(13):5399–5407 (1986).

Khrapko et al., "An oligonucleotide hybridization approach to DNA sequencing" *FEBS. Letters* 256(1,2):118–122 (1989).

Kleinfeld, D., "Controlled Outgrowth of Dissociated Neurons on Patterned Substrates" *J. Neurosci.* 8(11):4098–4120 (1988).

Kyser et al., "Design of an impulse ink jet" *J. Appl. Photographic Eng.* 7:73–79 (1981).

L'opez et al., "Imaging of features on surfaces by condensation figures" *Science* 260(5108):647–649 (1993).

Maskos & Southern, "Oligonucleotide hybridisations on glass supports: A novel linker for oligonucleotide synthesis and hybridisation properties of oligonucleotides synthesized in situ" *Nucleic Acids Res.* 20(7):1679–1684 (1992).

Maskos and Southern, "A novel method for the analysis of multiple sequence variants by hybridisation to oligonucleotides" *Nucleic Acids Res.* 21(9):2267–2268 (1993).

McBride and Caruthers, "An investigation of several deoxynucleoside phosphoramidites useful for synthesizing deoxyoligonucleotides" *Tetrahedron Lett* 24:245–248 (1983).

Pease et al., "Light–generated oligonucleotide arrays for rapid DNA sequence analysis" *Proc. Natl. Acad. Sci. USA* 91(11):5022–5026 (1994).

Southern et al., "Analyzing and comparing nucleic acid sequences by hybridization to arrays of oligonucleotides: evaluation using experimental models" *Genomics* 13(4):1008–1017 (1992).

Southern et al., "Arrays of complementary oligonucleotides for analysing the hybridisation behaviour of nucleic acids" *Nucleic Acids Res.* 22(8):1368–1373 (1994).

Takahashi et al., "Full color ink–jet printer" *NEC Res. and Develop.* 80:38–41 (1986).

Xu et al., "Use of 1,2,4–dithiazolidine–3,5–dione (DtsNH) and 3–ethoxy–1,2,4–dithiazoline–5–one (EDITH) for synthesis of phosphorothioate–containing oligodeoxyribonucleotides" *Nucleic Acids Research* 24(9):1602–1607 (1996).

Derwent Publications Ltd., London, GB; Section Ch. Week 9717, Abstract XP002101310 and JP 09 048938 (Fuji Film Co. Ltd.), Feb. 1997.

SOLVENT FOR OLIGONUCLEOTIDE SYNTHESIS AND METHODS OF USE

BACKGROUND OF THE INVENTION

The invention relates to solvents useful for oligonucleotide synthesis and to the use of such solvents for assembling an array of oligonucleotides on a support surface.

The genetic information generated by the Human Genome Project is allowing scientists, physicians, and others to conduct diagnostic and experimental procedures on an unprecedented scale in terms of speed, efficiency, and number of screenings performed within one procedure. In order to make full use of the new information, there is an urgent need for the ability to screen a large number of oligonucleotide probes against samples of DNA or RNA from normal or diseased cells and tissue. One important tool for such analyses is nucleic acid hybridization, which relies on the difference in interaction energies between complementary versus mismatched nucleic acid strands. Using this tool, it is possible to determine whether two short pieces of nucleic acid are exactly complementary. Longer nucleic acids can also be compared for similarity.

Nucleic acid hybridization is often used in screening cloned libraries to identify similar, thus presumably related, clones. This procedure typically involves natural nucleic acid targets which are usually bound to a membrane, and a natural or synthetic nucleic acid probe, which is washed over many targets at once. With the appropriate mechanics, membranes can be constructed with targets at a density of between one and ten targets per $mm^2$. Hybridization detection is carried out by labeling the probe, either radioactively or with chemiluminescent reagents, then recording the probe's emissions with film.

Alternative approaches to that described above for nucleic acid hybridization have attempted to employ an array of oligonucleotide probes synthesized on a solid support and then hybridized to a single natural target. These alternative approaches have yielded systems for assembling an array of oligonucleotides on a large scale, but the cost of making a variety of arrays is prohibitive.

For example, Brennan, U.S. Pat. No. 5,474,796, describes a piezoelectric impulse jet pump apparatus for delivering oligonucleotide synthesis reagents to array plates. The array plate is held in a mechanical stage that can be moved along the X and Y directions to position the plate under the appropriate jet nozzle. A separate nozzle head is provided for each of the four nucleotide monomers, and a fifth head delivers an activating reagent for synthetic coupling. Brennan describes that the solvents of choice for synthetic coupling in the jet pump apparatus are acetonitrile and diethylglycol dimethyl ether. Successful operation of the apparatus is not shown since the patent contains no data on the synthesis and assembly of multiple oligonucleotides.

Baldeschwieler (WO 95/25116) similarly describes an automated system for delivering oligonucleotide synthesis reagents to a substrate on which an array of oligonucleotides is produced. The patent envisions a five jet system, with one jet for each of the four nucleotide reagents, and one jet for the activating tetrazole solution. The movement of the device across the X and Y axis is computer-controlled, with the ink jet delivering reagent upwards to the underside of a microscope slide. According to Baldeschwieler, suitable solvents for the automated system include dibromomethane, nitromethane, acetonitrile, and dimethyl formamide. The deprotection reagent is 0.8 M ZnBr2 in 9:1 nitromethane:isopropanol.

Baldeschwieler also provides a description of the use of the ink jet system to synthesize an oligonucleotide. However, in contrast to the envisioned automated system, the ink jet was only used for delivery of the deprotecting agent. The 4×5 arrays of poly-T oligonucleotides were instead synthesized using a standard phosphoramidite synthetic cycle. The slide was exposed to the phosphoramidite monomers dissolved in acetonitrile in a reaction trough. Successive cycles of deprotection were carried out using the ink jet nozzle to apply the deprotection agent. However, the phosphoramidite monomers were added by exposing the slide to reaction solution in a trough, not by application using the ink jet nozzles.

Thus, automated application of nucleotides in solution to specific addresses on a matrix, using an ink jet nozzle system was not demonstrated by Brennan and/or by Baldeschwieler. There is no evidence that either system was operational for its intended purpose. In each case acetonitrile was a preferred solvent for nucleotide phosphoramidites, but in Baldeschwieler's working example, the matrix was exposed to the nucleotides in acetonitrile in a trough, not by ink jet application.

The solvent acetonitrile has several disadvantages that render it unsuitable for use in these automated systems. Acetonitrile has a low boiling point (81° C.) and evaporates quickly at room temperature. This causes problems with the drops evaporating before the necessary chemical reactions have gone to completion. Evaporation of acetonitrile at the nozzle causes the solutes to crystallize out and clog the nozzle. Acetonitrile also has a low surface tension of about 29 dynes per cm. This low surface tension causes it to wet the face of the nozzle and leads to unstable drop formation. Also, acetonitrile is incompatible with several materials, such as glues and plastics, used in commercial ink-jet printer heads.

Thus, there exists a need for a method of synthesizing an array of oligonucleotides on a solid support, wherein the oligonucleotides remain bound to the support, or are removed for subsequent applications. In particular, there exists a need for a solvent suitable for use in the automated synthesis of the oligonucleotide arrays. The present invention satisfies this need and provides related advantages as well.

SUMMARY OF THE INVENTION

The invention provides a method of oligonucleotide synthesis. The method consists of chemically coupling a first nucleotide monomer to a second nucleotide monomer in a high surface tension solvent. Synthesis can be performed either through the coupling of the 5' position of the first monomer to the 3' position of the second monomer or vice versa. The high surface tension solvent can be, for example, propylene carbonate and can be used in a variety of nucleotide coupling reactions including, for example, phosphodiester, phosphotriester, phosphite triester or phosphoramidite and H-phosphonate chemistries. Additionally, the high surface tension solvent can be used with deoxyribonucleotide or ribonucleotide monomers as well as with modified nucleotides or nucleotide derivatives. The high surface tension solvent can be used with iterative coupling cycles to synthesize oligonucleotides of a desired length and sequence.

Also provided is a method of oligonucleotide synthesis using a high surface tension solvent wherein the synthesis is automated. Automated synthesis can be performed on a solid support such as glass beads or a flat planer surface. Two dimensional arrays of oligonucleotide populations are also provided. Automated assembly of the oligonucleotides into the two dimensional array can be performed using an ink-jet pump apparatus to deliver the first and second nucleotide monomers to a specified position on a solid support. The oligonucleotide arrays can be used while attached to the support, or the population of oligonucleotides can be detached and used in solution.

According to one method, the invention provides successive solutions of chemical reactants, specifically nucleotide monomers, which are added to functionalized binding sites on a support surface. The method involves covalent attachment of an organic linker molecule to a surface, followed by building the oligonucleotide off the end of the linker through a series of coupling and deprotection steps. The sequence of the oligonucleotide is determined by which of the four nucleotide monomers is added during each coupling step. During the reaction steps, the oligonucleotide remains covalently bound to the surface.

In one embodiment, the invention provides a method of step-by-step synthesis of an array of different chemical compounds at microdropsized loci, where each compound is covalently attached to the surface of a substrate, comprising the steps of:

(a) applying through a single unit of a multiple reagent dispenser at least one microdrop of a first reagent dissolved in propylene carbonate to said surface, wherein said substrate is chemically prepared to react with said first reagent to covalently attach said reagent to said substrate;

(b) displacing said multiple reagent dispenser relative to said surface, or the surface with respect to multiple reagent dispenser, and applying at least one microdrop containing either the first reagent or a second reagent dissolved in propylene carbonate from the same or a different dispenser unit to said surface wherein said substrate is chemically prepared to react with said reagent to covalently attach said reagent to said substrate;

(c) optionally repeating step (b) at least one time using the same or different reagents dissolved in propylene carbonate from different dispenser units wherein each of said reagents covalently attaches to said substrate to form covalently attached compounds;

(d) washing said substrate to remove unattached reagents;

(e) modifying said attached reagents so as to allow covalent coupling with a second reagent; and (f) repeating steps (a) through (e) with the same or different reagents dissolved in propylene carbonate at various loci on the substrate.

In a specific embodiment, the chemical is an oligonucleotide, and the reagents are nucleotide monomers or tetrazole, or various derivatives such as 5-ethylthio-1H-tetrazole, which activate the nucleotide monomers for the coupling reaction. The nucleotide monomers can be, for example, nucleotide phosphoramidites.

In these embodiments, a high surface tension solvent for the nucleotide monomers can be, for example, propylene carbonate, which has a high boiling point, high viscosity, and high surface tension. These characteristics make propylene carbonate suitable for use in, for example, a microfabricated ink-jet pump apparatus. Other solvents having these characteristics are also suitable.

BRIEF DESCRIPTION OF THE DRAWINGS

FIG. 1 (bottom) shows a side view of a surface tension well showing the arrangement of hydrophilic and hydrophobic regions.

DETAILED DESCRIPTION OF THE INVENTION

Figure 1A:
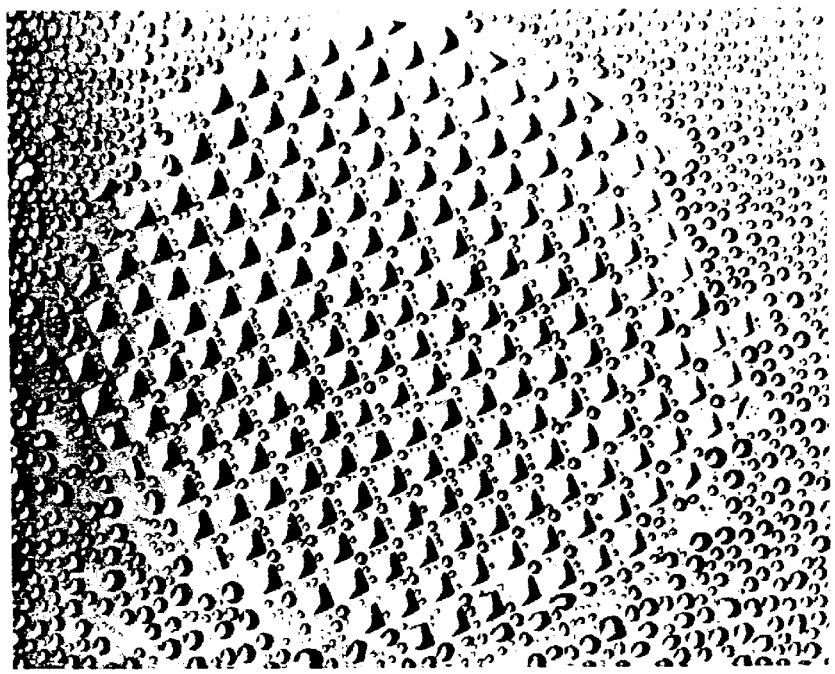
FIG. 1 (top) shows a photograph of water condensed onto an array of approximately 250 surface tension wells. Individual droplets are confined to square regions of 100 micron sides by 30 micron wide hydrophobic barriers.

The invention is directed to a method of oligonucleotide synthesis using a high surface tension solvent such as propylene carbonate. This solvent exhibits the additional characteristics of having a high boiling point and a high viscosity and is capable of supporting nucleotide coupling reactions. Propylene carbonate is advantageous in the use of nucleotide coupling reactions because, unlike acetonitrile and other strong solvents, it does not destroy or degrade a variety of synthetic polymers. Therefore, propylene carbonate can be used in procedures for automated oligonucleotide synthesis which employ the use of plastic parts in contact with nucleotide synthesis reagents. Thus, the method allows for the automated synthesis of oligonucleotide arrays using ink jet nozzles for the delivery of reactants to a substrate surface.

As used herein, the term "high surface tension solvent" when used in reference to chemical coupling reactions is intended to mean a solvent which exhibits a surface tension of about 30 dynes/cm or more and supports reaction cycles involving monomer addition to the growing end of an oligopolymer. The high surface tension solvents of the invention are also compatible for use with synthetic polymers such as plastics so they can be used in automated devices for synthesis or sequencing of biopolymers. A specific example of a high surface tension solvent exhibiting these characteristics is propylene carbonate. Beneficial properties of propylene carbonate include a surface tension of 41.1 dynes/cm, a viscosity of 2.5 centipoise and a boiling point of 240° C. In comparison, acetonitrile exhibits a surface tension of 29.0 dynes/cm, a viscosity of 0.375 centipoise and a boiling point of 81° C. Other solvents that can be suitable include, for example, ethylene carbonate, hexamethylphosphoric triamide (HMPA), and dimethyl sulfoxide.

Generally, suitable solvents can have the structure

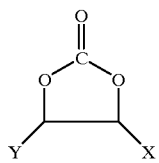

wherein X and Y are each one of the following group: H, $CH_3$, $C_2H_5$, $C_3H_7$, $C_4H_9$.

As used herein, the term "substrate" when used in reference to a solid support is intended to mean a generally flat surface, porous or not, which has, or can be chemically modified to have, reactive groups suitable for attaching further organic molecules. Examples include: glass, silica, silicon, polyproplyene, Teflon, polyethylimine, nylon, fiberglass, paper, and polystyrene. The surface may also consist of bead structures attached to a solid surface, wherein the beads are composed of one or more of the preceding materials.

The invention provides a method of oligonucleotide synthesis in a high surface tension solvent. The method consists of chemically coupling a first nucleotide monomer with a second monomer or an oligonucleotide in the high surface tension solvent under conditions which allow covalent bond formation between the first and second monomer or between the first monomer and the oligonucleotide. The covalent bond formation joins the 5' position of the first nucleotide monomer with the 3' position of the second nucleotide monomer so as to form an oligonucleotide product. Alternatively, coupling can proceed in the opposite direction. Nucleotide linkages other than between the 5' and 3' positions of nucleotide monomers also exist and can be synthesized by methods known to those skilled in the art. For example, synthesis methods exist for the covalent bond formation between the 5' positions of two nucleotide monomers, or between the 5' position of a nucleotide monomer and the 5' position of an oligonucleotide chain. Similarly, synthesis methods exist for the covalent bond formation between the 3' positions of two nucleotide monomers, or between the 3' position of a nucleotide monomer and the 3' position of an oligonucleotide chain. In addition, reagents for synthesizing all of the above linkages using a variety of chemistries are commercially available and are known to those skilled in the art.

Oligonucleotide synthesis in a high surface tension solvent can be performed, for example, using any of a variety of chemistries and methods known to those skilled in the art. The choice of which chemistry to use with the high surface tension solvents of the invention will depend on the particular application and preference of those in the field of oligonucleotide chemistry. As will be described below, the methods described herein employing high surface tension solvents in oligonucleotide coupling reactions can be used with known chemistries by substituting a known coupling buffer or solvent with a high surface tension solvent.

Briefly, synthesis of oligodeoxyribonucleotides requires the specific and sequential formation of internucleoside 3'–5' or 5'–3' phosphodiester linkages. In order to form these specific linkages between two 2'-deoxyribonucleoside monomers, or between a monomer and the growing end of an oligonucleotide, the nucleophilic centers not involved in the linkage must be chemically protected through the use of protecting groups. Additionally, one of the two monomers must be phosphorylated or phosphitylated on the only available hydroxyl group and then coupled to the other nucleoside unit in a chemical coupling reaction. The resultant dinucleoside monophosphate commonly carries a protecting group on the phosphate introduced during the phosphorylation (or phosphitylation) step, such that the internucleoside phosphate becomes a triester. To extend the chain, one of the two terminal protecting groups must be removed selectively to generate a free hydroxyl function to which a new partially protected unit can be joined.

Solid phase methods use an insoluble polymeric or inorganic support as one of the protecting groups. This protecting group is commonly referred to as a permanent protecting group because it must remain stable throughout the assembly and can be removed at the end of the synthesis in order to generate the final deprotected oligonucleotide. The protecting group removed after each coupling step is referred to as a temporary protecting group.

Protecting groups are introduced by methods known to those skilled in the art. The selection of a particular protecting group is determined based on the particular chemistry used for the oligonucleotide synthesis. Chemistries available for oligonucleotide synthesis include, for example, phosphodiester, phosphotriester, phosphate triester or phosphoramidite and H-Phosphonate chemistry. These chemistries result in the synthesis of an oligonucleotide in the 3' to 5' direction. However, other chemistries known in the art which proceed in the opposite direction are equally applicable for oligonucleotide synthesis using the high surface tension solvents and methods described herein.

Briefly, the phosphodiester method of oligonucleotide synthesis involves coupling of a 5'-protected deoxynucleoside derivative with a 3'-protected deoxynucleoside-5'-phosphomonoester. Phosphotriester chemical coupling is where a 5'—O—(chlorophenyl phosphate) is coupled to a deoxynucleoside attached at its 3'-position to a solid support. Phosphate triester or phosphoramidite chemistry involves a coupling reaction between the 5'-hydroxyl group of a support-bound deoxynucleoside and an alkyl 5'-DMTr-(N-acylated)-deoxynucleoside 3'—O—(N,N-diisopropylamino)phosphite (the alkyl group being methyl or 2-cyanoethyl). H-Phosphonate couplings involve a deoxynucleoside 3'—O—(H-phosphonate) as a tetracoordinated species. Such chemistries and their respective protecting groups are known to those skilled in the art and can be found described in, for example, Blackburn and Gait (eds.), *Nucleic Acids in Chemistry and Biology*, Second Edition, New York: Oxford University Press (1996).

Assembly of oligonucleotide chains is most reproducibly accomplished using a commercial DNA synthesizer, but a manual flow system or even a small sintered glass funnel can be substituted in the methods of the invention. Although machine specifications can vary considerably, the basic steps involved in one cycle of nucleotide addition are set forth below for the specific example of using phosphoramidite chemistry. Therefore, the invention provides a method of oligonucleotide synthesis using a high surface tension solvent wherein the synthesis is automated and is performed on a solid support. The invention also provides for methods of oligonucleotide synthesis using a high surface tension solvent wherein synthesis is automated so as to produce a two dimensional array of a plurality of different oligonucleotides on a solid support.

The first step of oligonucleotide synthesis involves the detritylation or removal of dimethoxytrityl groups which is usually accomplished with dichloroacetic or trichloroacetic acid (TCA) in methylene chloride. Step two is the activation of the phosphoramidite which occurs when it is mixed with tetrazole in the nucleotide solvent. Step three, which can occur simultaneously with step two, is the addition of activated phosphoramidite to the growing chain whereas an optional step four is a procedure termed capping and is introduced to block chains which did not react during the previous coupling reaction. The final step involves the oxidation of the intermediate phosphite to the phosphotriester and can be achieved, for example, with iodine and water. The cycle can then be repeated the requisite number of times to achieve the desired length of oligonucleotide. Following synthesis, the oligonucleotide is deprotected and optionally removed from the support. Using the methods described herein, the high surface tension solvents are used at least during steps two and three.

In addition to the chemistries described above, alternative reactions can be used in the methods of the invention where modified nucleotides or nucleotide derivatives are synthesized into oligomers using the high surface tension solvents. Such modified nucleotides can include, for example, combinations of modified phosphodiester linkages such as phosphorothioate, phosphorodithioate and methylphosphonate as well as modified bases such as inosine, 5'-nitroindole and 3'-nitropyrrole.

Synthesis of oligoribonucleotides can similarly be accomplished using the methods and high surface tension solvents of the invention. Effective chemical methods for oligoribonucleotide synthesis have added complications resulting from the 2'-hydroxyl group in a ribonucleoside moiety. However, ribonucleotide coupling chemistries and protecting groups are available and well known to those skilled in the art. Therefore, such chemistries are applicable in the methods described herein.

As with oligodeoxyribonucleotides, a range of modifications can similarly be introduced into the base, the sugar, or the phosphate moieties by preparation of appropriately protected phosphoramidite or H-phosphonate ribonucleotide monomers, for example, and coupling such modified forms into oligoribonucleotides by solid-phase synthesis. Modified ribonucleotide analogues include, for example, 20'—O—methyl, 2'—O—allyl, 2'-fluoro, 2'-amino phosphorothioate, 2'—O—Me methylphosphonate, αribose and 2'-5'-linked ribonucleotide analogues.

For use of the above described high surface tension solvent in the automated synthesis of nucleotide arrays, one embodiment of the invention involves a system utilizing a mechanism for localizing and separating small (less than 100 pL) reagent droplets. At such small scales, surface tension is the strongest force acting on a droplet and can be used, for example, to create "surface tension wells" to constrain the droplets (FIG. 1). According to the invention, methods have been developed to produce an array of circular wells. The wells define the locations of the array elements, and act as miniature reaction vessels for oligonucleotide synthesis. The wells can vary in size and will depend on the intended use of the synthesized array. For example, the diameter of each well can be greater than 1000 microns but typically is between 1 and 1000, preferably between 10 and 500 and more preferably between 40 and 100 microns. Similarly, the separation of the wells will also vary according to the intended use of the array. Each well is typically separated by between about 1 to 500 microns. Preferably, separations are between about 10 to 100 and more preferably between about 20–30 microns. Those skilled in the art will know or can determine what is the applicable size and separation of wells within an array for a particular use.

Methods known in the art can be used to create the array of circular wells. Such methods can involve the creation of hydrophilic wells by first applying a protectant, or resist, over each well within the array area. The unprotected area is then coated with a hydrophobic agent to yield an unreactive surface. For example, a hydrophobic coating can be created by chemical vapor deposition of (tridecafluorotetrahydrooctyl)-triethoxysilane onto the exposed oxide surrounding the protected circles. Finally, the protectant, or resist, is removed exposing the well regions of the array for further modification and nucleotide synthesis using the high surface tension solvents described herein and procedures known in the art such as those described by Maskos & Southern, *Nuc. Acids Res.* 20:1679–1684 (1992). Arrays produced in such a manner can localize small volumes of solvent within the circular wells by virtue of surface tension effects (L'opez et al., *Science* 260:647–649 (1993)).

The protectant, or resist, can be applied in an appropriate pattern by, for example, a printing process using a rubber stamp, a silk-screening process, an ink-jet printer, a laser printer with a soluble toner, evaporation or by a photolithographic process, such as that reported by Kleinfeld, D., *J. Neurosci.* 8:4098–4120 (1988). The hydrophobic coating can also be applied directly in he appropriate pattern by, for example, a printing process using a rubber stamp, a silk-screening process, or laser printer with a hydrophobic toner.

Additionally, the use of high surface tension solvents allows for the direct synthesis of oligonucleotide arrays onto the silicon wafer without creating hydrophilic wells. Such direct synthesis can be accomplished by, for example, accurately applying the synthesis reagents to each loci which constitute the wells of the array. Automated ink-jet nozzle heads can be used for accurately applying the synthesis reagents in either single or multiple dispenser format. The use of such ink jet nozzles is described further below.

Figure 2:
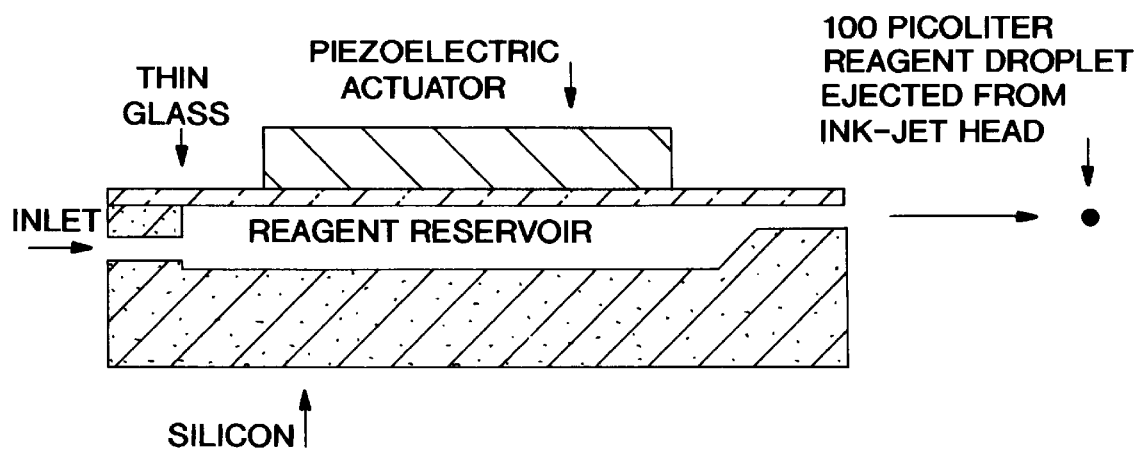
FIG. 2 shows a schematic diagram of an ink-jet pump. A transient voltage applied to the piezoelectric actuator causes the thin glass membrane to bow inwards. This results in a small droplet being ejected from the nozzle. The reservoir refills itself through the inlet by capillary action.

The method of the invention also entails delivery of small amounts of synthesis reagents to the appropriate wells. In one embodiment, microfabricated ink-jet pumps, or nozzles, similar to those used in ink-jet printers are used to deliver specified volumes of synthesis reagents to the array of surface tension wells (Kyser et al., *J. Appl. Photographic Eng.* 7:73–79 (1981)). The pumps are made by using etching techniques known to those skilled in the art to fabricate a shallow cavity and channels in silicon. A thin glass membrane is then anodically bonded to the silicon to seal the etched cavity, thus forming a small reservoir with narrow inlet and exit channels (FIG. 2). When the inlet end of the pump is dipped in the reagent solution, capillary action draws the liquid into the cavity until it comes to the end of the exit channel. When an electrical pulse is applied to the piezoelectric element glued to the glass membrane it bows inward, ejecting a droplet out of the orifice at the end of the pump. Simple designs for ink-jet pumps will operate at 1 kHz, while more advanced designs operate at 6 kHz (Takahashi et al., *NEC Res. and Develop.* 80:38–41 (1986)).

For oligonucleotide synthesis in two dimensional arrays, pumps that will deliver 100 pl droplets or less on demand at rates of several hundred Hz are applicable. However, the droplet volume or speed of the pump can vary depending on the need. For example, if a larger array is to be synthesized with the same surface area, then smaller droplets should be dispensed. Additionally, if synthesis time is to be decreased then operation speed can be increased. Such parameters are known to those skilled in the art and can be adjusted according to the need.

Figure 3:
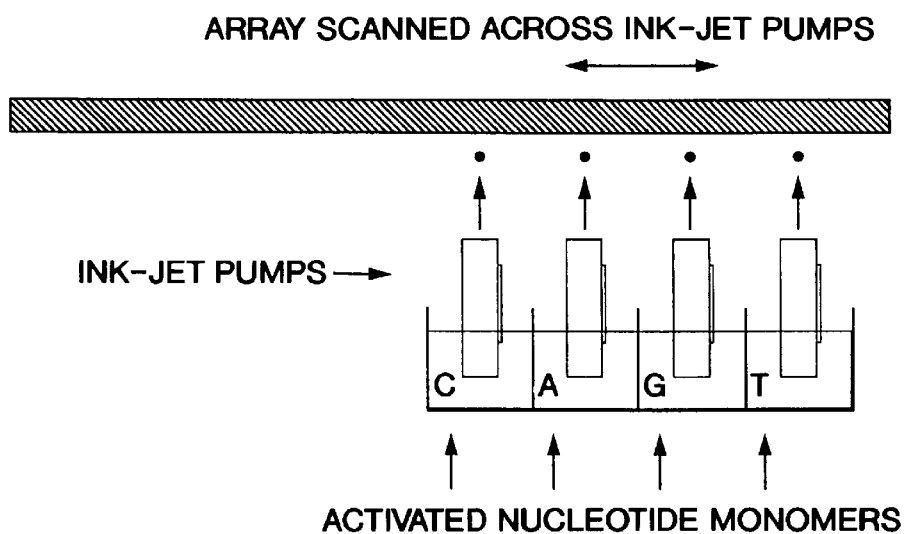
FIG. 3 shows a computer, in conjunction with an x-y stepping stage, which coordinates the firing of the ink-jet pumps with the motion of the array to deliver the correct nucleotide to each surface tension well.

Using the above methods, the array is scanned across a set of pumps using a computer-controlled x-y translation stage (FIG. 3). The computer synchronizes and times the firing of the pumps to deliver a single droplet of the appropriate reagent to each well with the array.

Figure 4:
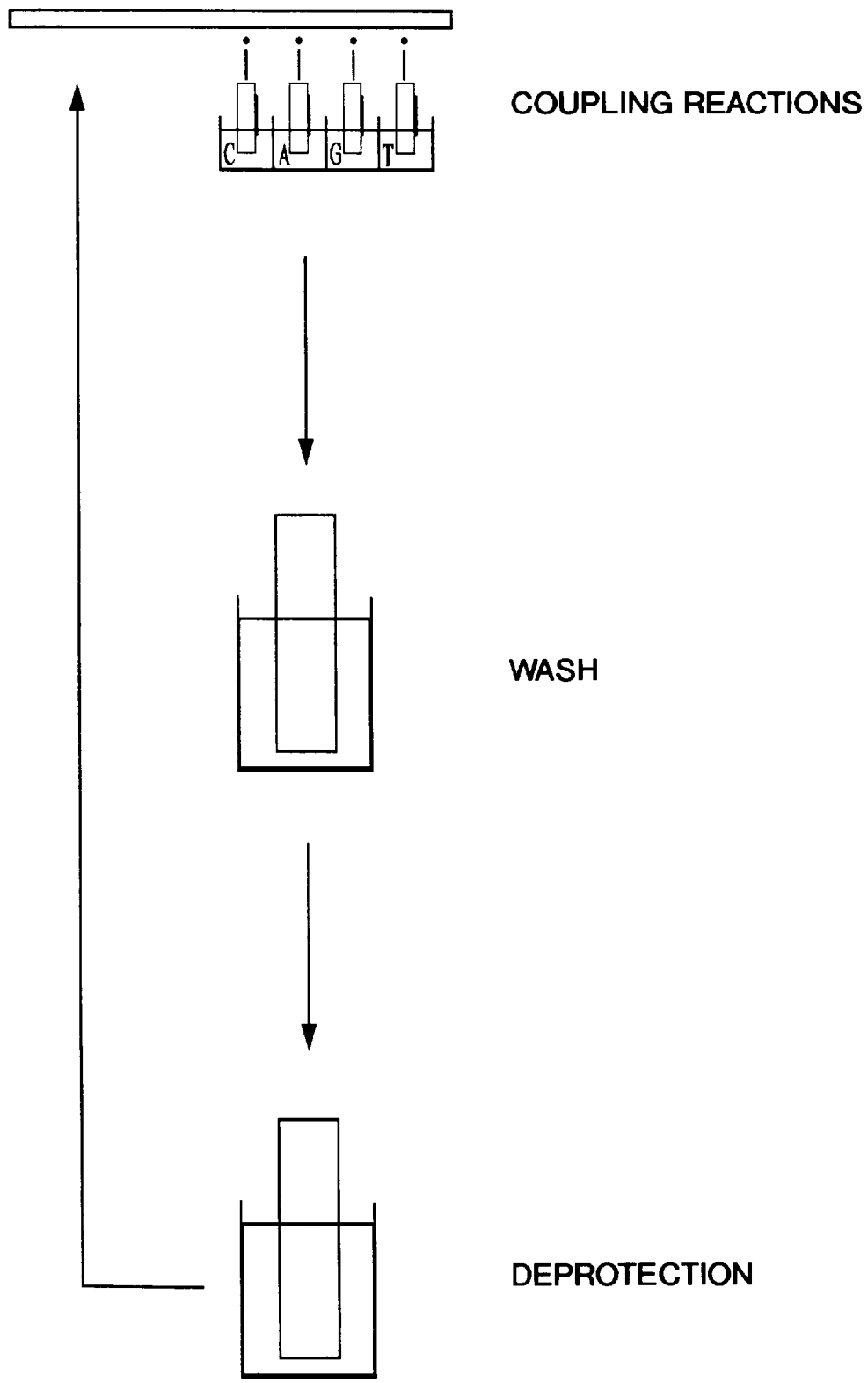
FIG. 4 shows a complete cycle of DNA synthesis consists of delivering the correct nucleotide to each well, washing away unreacted nucleotide monomers, and deprotecting the ends of the extended molecules. Each cycle adds one nucleotide to each position on the array, thus an array of 25 monomers would require 25 such cycles.

A complete synthesis cycle starts by delivering the appropriate nucleotide monomer along with an activator such as tetrazole either pre-mixed with the monomer, or separately from a separate nozzle, to each well on the wafer (FIG. 4). The entire wafer is rinsed to remove excess monomer exposed to an oxidizing solution, typically an iodine/tetrahydrofuran/pyridine/water mixture, then rinsed with acid to deprotect the end of the oligonucleotide in preparation for the next round of synthesis. The rinses are common to all the wells and can be done, for example, by bulk immersion. One such cycle adds one nucleotide to each oligonucleotide, thus a wafer of oligonucleotides having a length of ten nucleotides requires 10 such cycles.

The number of cycles, and therefore, the length of the oligonucleotides, will be determined by the need and desired use of the array. As such, the oligonucleotide lengths which can be achieved using the methods of the invention are only limited by the existing coupling chemistries. Routinely, oligonucleotides between 10 and 100, and preferably between 20 and 60 nucleotides in length can be synthesized. As coupling chemistries advance, so will the yield and length of oligonucleotide products. Therefore, it is envisioned that the methods of the invention are useful for the synthesis of oligonucleotide arrays where each oligonucleotide has a length of greater than 100 nucleotides.

Ink-jet printers generally contain heads with approximately 100 independently controlled pumps. With each pump operating at several hundred Hz, a machine with five such heads can deliver the appropriate reagents to 100,000 wells in a matter of seconds. A complete synthesis cycle can take, for example, 5 minutes, or just over 2 hours for an array of 100,000 oligonucleotides having 25 nucleotide residues. Ink-jet heads having more or less pumps and which operate at different speeds can be used as well. Additionally, multiple heads can be simultaneously used to synthesize the oligonucleotide arrays. Such modifications are known to those skilled in the art and will vary depending on the size, format and intended use of the assay.

While the present disclosure is described using nucleotide arrays as an example, the methods of the invention can be applied to other chemistries that rely on cycles of coupling and deprotection. It is possible to construct arrays of peptides, or other heteromeric polymers with sequence dependent properties, using the methods of the invention. For example, to synthesize polypeptides, a linker molecule is provided as the first reagent whereby one end of the linker is attached to the substrate surface. The other end of the linker is adapted to form a linkage with the carboxy terminal of an amino acid or peptide, to form, for example, an amide or ester linkage. This end of the linker can be initially chemically protected by protecting groups such as t-butoxycarbonyl groups (t-BOC) or other protecting groups known in the peptide synthesis art. By application of a second reagent onto the locus which removes a protecting group, such as an acid solution, the protecting group can be removed. The next reagent applied at each locus is then an amino terminal-protected and side-chain protected amino acid or polypeptide, preferably having an activated C-terminal group for linking the C-terminal to the end of the linker. This process can be repeated with the same or different amino acids or peptides at each of the microdrop loci until the substrate includes the peptides of desired sequences and lengths. Thereafter, the protective groups are removed from some or all of the peptides, as desired. Deprotection can be achieved using, for example, a common deprotection agent which removes the protecting groups on side chains and the amino ends simultaneously, as is known in the peptide synthesis art. The peptides can be cleaved from the linker using methods known to those of ordinary skill in the peptide synthesis art which cleave peptides from a solid support as, for example, used in the Merrifield synthesis technique.

It will be realized that a particular advantage of this method is that, by keeping a record of the reagents utilized at each of the microdrop sized loci, peptides of different lengths and sequences can be made concurrently on the same substrate. Such peptides can have a variety of uses including, but not limited to, screening for biological activity whereby the respective peptide sequences at each locus is exposed to a labeled or unlabeled peptide receptor, such as an antibody, a cell receptor, or any other variety of receptor.

The synthesis and assembly of oligonucleotide arrays using the high surface tension solvents and methods of the invention are described further below in Example II. The synthesis and assembly of oligonucleotide arrays can additionally be carried out using a ink-jet pump apparatus and the general methods described by, for example, Brennan, U.S. Pat. No. 5,474,796, and Baldeschweiler WO 95/25116, both of which are incorporated herein by reference.

Thus, the invention also describes a method of step-by-step synthesis of an array of different chemical compounds at microdropsized loci where each compound is covalently attached to the surface of a substrate. The method consists of (a) applying through a single unit of a multiple reagent dispenser at least one microdrop of a first reagent dissolved in propylene carbonate to said surface, wherein said substrate is chemically prepared to react with said first reagent to covalently attached said reagent to said substrate; (b) displacing said multiple reagent dispenser relative to said surface, or the surface with respect to multiple reagent dispenser, and applying at least one microdrop containing either the first reagent or a second reagent dissolved in propylene carbonate from a different dispenser unit to said surface wherein said substrate is chemically prepared to react with said reagent to covalently attach said reagent to said substrate; (c) optionally repeating step (b) at least one time using the same or different reagents dissolved in propylene carbonate from different dispenser units wherein each of said reagents covalently attaches to said substrate to form covalently attached compounds; (d) washing said substrate to remove unattached reagents; (e) modifying said attached reagents; and (f) repeating steps (a) through (e) at least once with the same or different reagents dissolved in propylene carbonate at various loci on the substrate. Using the above method, a plurality of different chemical compounds within the array can be simultaneously synthesized having lengths in excess of 100 monomers in length.

It is understood that modifications which do not substantially affect the activity of the various embodiments of this invention are also included within the definition of the invention provided herein. Accordingly, the following examples are intended to illustrate but not limit the present invention.

EXAMPLE I

Propylene Carbonate Compared with Acetonitrile as Solvent for Oligonucleotide Synthesis This Example compares the oligonucleotide coupling efficiency of a high surface tension solvent to that of acetonitrile.

Propylene carbonate is an appropriate solvent for assembly of oligonucleotides, with a yield comparable to that of acetonitrile. Eight separate oligonucleotide homopolymers of eleven nucleotides in length of A, T, C and G were assembled using either propylene carbonate or acetonitrile. Synthesis proceeded using an Applied Biosystems model 380B automated synthesizer and phosphoramidite chemistry according to the manufacturer. The Trityl assay was used to estimate stepwise yields on all eight syntheses. This assay is measures the amount of dimethoxytrityl released during the deprotection step of the synthetic cycle. The measurement is conveniently carried out photometrically since dimethoxytrityl absorbs light strongly at 498 nm. Using this assay, an estimate of the efficiency of the synthetic reactions was made by comparing the amounts of dimethoxytrityl released from one cycle to the next. The results are summarized below in Table 1 and show comparable yields for synthesis in acetonitrile and propylene carbonate.

TABLE 1

Assembly of oligonucleotide homopolymers using acetonitrile or propylene carbonate

| % yield | polydT | | polydG | | polydA | | polydC | |
| --- | --- | --- | --- | --- | --- | --- | --- | --- |
| | A* | PC | A | PC | A | PC | A | PC |
| Average | 99.4 | 99.6 | 99.3 | 97.4 | 97.8 | 96.6 | 98.9 | 98.4 |
| Overall | 88.8 | 89.4 | 87.6 | 74.1 | 77.6 | 65.9 | 88.8 | 85.4 |
| Stepwise | 98.8 | 98.9 | 98.7 | 97.0 | 97.5 | 95.9 | 98.8 | 98.4 |

*A = Acetonitrile; PC = Propylene Carbonate

EXAMPLE II

Synthesis of Two-Dimensional Oligonucleotide Arrays

This Example describes the automated synthesis of a two-dimensional array of oligonucleotides.

For synthesis of a two-dimensional array, a standard glass microscope slide, 25 mm×75 mm, was used as the solid support for which to assemble the growing arrays. The slide was first derivitized by treating with glycidoxypropyl silane and tetraethylene glycol according to the procedures of Southern et al. (E. M. Southern, U. Maskos, J. K. Elder, "Analyzing and comparing nucleic acid sequences by hybridization to arrays of oligonucleotides: evaluation using experimental models" *Genomics* 13(4):1008–1017 (1992). The derivitized slide was then attached to an X-Y translation table driven by two stepper motors via a lead screw.

Four ink jets, mounted beside the X-Y translation table and below the microscope slide were used for delivery of the nucleotide monomers and synthesis reagents. The ink jets were of the type used in the "StylusColor II" printer sold by the Epson Corporation. Each of the ink jets were filled with a 0.1 molar solution of one of the four nucleotide phosphoramidites (A, C, T, G). The nucleotide phosphoramidites were dissolved in propylene carbonate while a fifth ink jet was filled with 0.5 molar solution of 5-ethylthio tetrazole in propylene carbonate.

A computer, along with the appropriate electronic interface, was used to synchronize the firing of the ink jets with the motion of the X-Y table to deliver one 42 pL drop of the 5-ethylthio tetrazole solution and one 42 pL drop of the appropriate nucleotide phosphoramidite solution to each region of synthesis on the glass slide. The reaction was allowed to proceed for 30 to 60 seconds under an inert atmosphere, such as dry nitrogen. This constituted the coupling step of the synthetic procedure.

The slide was rinsed with acetonitrile to remove excess reagents, then dipped for 30 seconds into an oxidizing solution consisting of iodine, pyridine and water. After rinsing again in acetonitrile, the slide was dipped for 60 seconds in a deblocking solution of 2.5% dichloroacetic acid in dichloromethane. After a final rinse in acetonitrile and drying in a stream of dry nitrogen, the slide was ready to continue the cycle with another coupling step.

After several, typically 20, such cycles the slide was then dipped in undiluted ethanolamine for 20 minutes at room temperature to remove the base protecting groups and the cyanoethyl groups on the phosphate linkages. After rinsing in ethanol then acetonitrile, the slide is ready for use.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A method of step-by-step synthesis of an array of different chemical compounds at loci, where each compound is covalently attached to a substrate, comprising the steps of:

(a) applying through an inkjet pump at least one microdrop of a first reagent dissolved in a solvent to the surface of said substrate at a first locus, wherein said substrate is chemically prepared to react with said first reagent to covalently attach said first reagent to said substrate, wherein said solvent has the structure

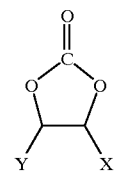

wherein X and Y are each one of the following groups: H, $CH_3$, $C_2H_5$, $C_3H_7$, and $C_4H_9$;

(b) displacing said inkjet pump relative to said surface, or the surface with respect to said inkjet pump, and applying at least one microdrop containing either the first reagent or a second reagent dissolved in said solvent from a different inkjet pump to a second locus of said surface wherein said substrate is chemically prepared to react with said first reagent or said second reagent to covalently attach said first reagent or said second reagent to said substrate;

(c) optionally repeating step (b) at least one time using the same or different reagents dissolved in said solvent at a locus of said surface different from said first and second loci;

(d) washing said substrate to remove unattached reagents;

(e) modifying said attached reagents; and (f) repeating steps (a) through (c), and optionally steps (d) through (e), at least once with the same or different reagents dissolved in said solvent at one or more of said loci.

2. The method of claim 1, wherein said chemical compound is an oligonucleotide and said reagents are nucleotide monomers.

3. The method of claim 1, wherein said steps (c) through (e) are repeated between 2 or more times.

4. The method of claim 1, wherein the substrate is porous.

5. The method of claim 2, wherein the substrate is porous.

6. The method of claim 3, wherein the substrate is porous.

7. The method of any of claims 1, 2, 3, 4, 5, or 6 wherein said solvent is propylene carbonate.

8. The method of any of claims 1, 2, 3, 4, 5, or 6 wherein said solvent is ethylene carbonate.

* * * * *

UNITED STATES PATENT AND TRADEMARK OFFICE
CERTIFICATE OF CORRECTION

PATENT NO. : 6,028,189

DATED : February 22, 2000

INVENTOR(S) : Blanchard

It is certified that error appears in the above-identified patent and that said Letters Patent is hereby corrected as shown below:

In column 1, before "BACKGROUND OF THE INVENTION", please insert --This invention was made with government support under NSF Grant Number BIR 9214821. The Government has certain rights in this invention.--.

In column 3, line 67, please delete "FIG. 1" and replace therefor with --FIG. 1a--.

Figure 1B:
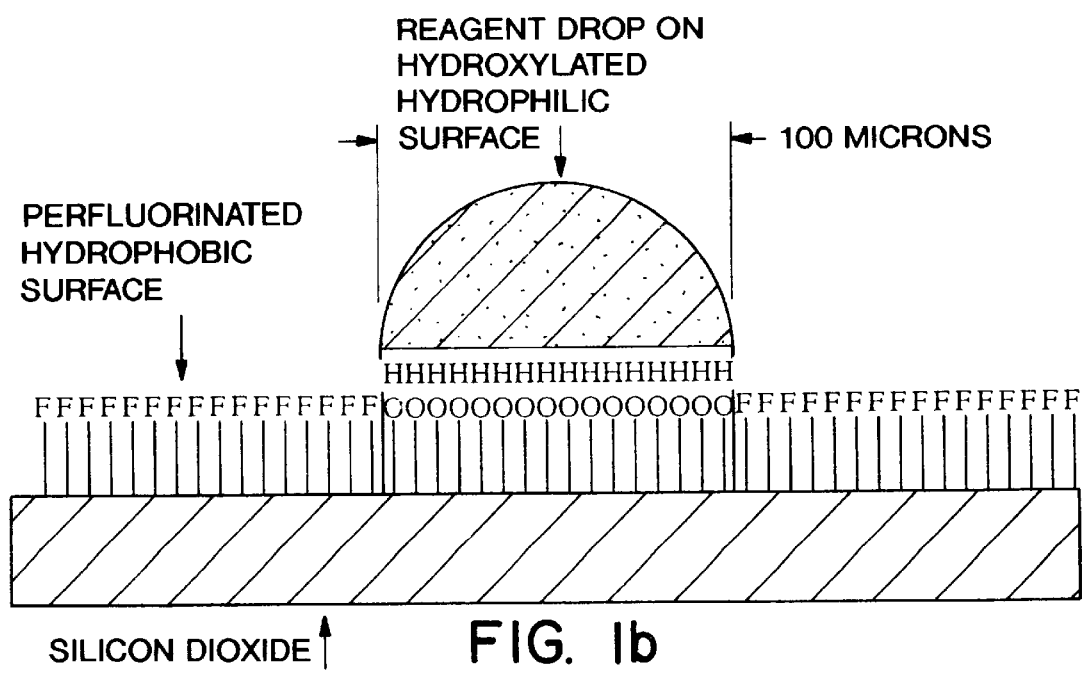

In column 4, line 2, please delete "FIG. 1" and replace therefor with --FIG. 1b--.

In column 7, line 38, please delete "20'" and replace therefor with --2'--.

In column 7, line 40, please delete "αribose" and replace therefor with --α-ribose--.

In column 8, line 21, please delete "he" and replace therefor with --the--.

UNITED STATES PATENT AND TRADEMARK OFFICE
CERTIFICATE OF CORRECTION

PATENT NO. : 6,028,189

DATED : February 22, 2000

INVENTOR(S) : Blanchard

It is certified that error appears in the above-identified patent and that said Letters Patent is hereby corrected as shown below:

In column 8, line 54, please delete "pl" and replace therefor with --pL--.

In column 11, line 7, please delete the word "is".

Signed and Sealed this

Seventeenth Day of April, 2001

Attest:

NICHOLAS P. GODICI

*Attesting Officer*    *Acting Director of the United States Patent and Trademark Office*